(12) United States Patent
Ortega et al.

(10) Patent No.: US 10,806,375 B2
(45) Date of Patent: Oct. 20, 2020

(54) WEARABLE DEVICE AND METHODS OF USING THE SAME

(71) Applicants: Francisco Raul Ortega, Miami, FL (US); Naphtali David Rishe, Miami Beach, FL (US); Armando Bennett Barreto, Miami, FL (US)

(72) Inventors: Francisco Raul Ortega, Miami, FL (US); Naphtali David Rishe, Miami Beach, FL (US); Armando Bennett Barreto, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/585,395

(22) Filed: May 3, 2017

(65) Prior Publication Data

US 2018/0317770 A1   Nov. 8, 2018

(51) Int. Cl.
*A61B 5/11* (2006.01)
*A61B 5/0205* (2006.01)
*A61B 5/0488* (2006.01)
*A61B 5/024* (2006.01)
*A61B 5/00* (2006.01)
*A61B 7/00* (2006.01)
*G06F 3/01* (2006.01)
*G06F 3/0346* (2013.01)
*A41D 19/00* (2006.01)
*G06F 3/0354* (2013.01)

(52) U.S. Cl.
CPC ........ *A61B 5/1107* (2013.01); *A61B 5/02055* (2013.01); *A61B 5/02416* (2013.01); *A61B 5/0488* (2013.01); *A61B 5/6824* (2013.01); *A61B 5/6826* (2013.01); *A61B 7/006* (2013.01); *G06F 3/011* (2013.01); *G06F 3/014* (2013.01); *G06F 3/015* (2013.01); *G06F 3/017* (2013.01); *G06F 3/0346* (2013.01); *A41D 19/0027* (2013.01); *A61B 5/4266* (2013.01); *A61B 2562/0219* (2013.01); *A61B 2562/166* (2013.01); *G06F 3/03547* (2013.01); *G06F 2203/0331* (2013.01)

(58) Field of Classification Search
CPC ..... A61B 5/6806; A61B 5/681; A61B 5/6824; A61B 5/6825; A61B 5/6826
See application file for complete search history.

(56) References Cited

U.S. PATENT DOCUMENTS

| 4,748,987 A | * | 6/1988 | Barry | .................. A61F 2/72 600/586 |
| 2009/0326406 A1 | * | 12/2009 | Tan | .................. G06F 3/015 600/546 |
| 2013/0135223 A1 | * | 5/2013 | Shai | .................. G06F 3/014 345/173 |

(Continued)

*Primary Examiner* — Christopher A Flory
*Assistant Examiner* — Nathan A Baldwin
(74) *Attorney, Agent, or Firm* — Saliwanchik, Lloyd & Eisenschenk (57) ABSTRACT

Wearable devices and methods of using the same for inputting ambient conditions and the movement and bio-signals of a user to an external device are provided. The wearable device can include a finger sensor and a wrist sensor, wherein each includes an accelerometer, a gyroscope, and a compass. The compass can be a magnetometer. The wrist sensor can also include a power source, a computer, and a touchscreen.

20 Claims, 7 Drawing Sheets

(56) References Cited

U.S. PATENT DOCUMENTS

| | | | |
|---|---|---|---|
| 2014/0267024 A1* | 9/2014 | Keller | G06F 3/017 |
| | | | 345/156 |
| 2015/0220109 A1* | 8/2015 | von Badinski | G01P 15/00 |
| | | | 340/539.12 |
| 2015/0282713 A1* | 10/2015 | Fei | A61B 5/0059 |
| | | | 600/476 |
| 2015/0370326 A1* | 12/2015 | Chapeskie | G06F 3/015 |
| | | | 345/156 |
| 2016/0022220 A1 | 1/2016 | Lee et al. | |
| 2016/0041580 A1* | 2/2016 | Inoue | G06F 1/163 |
| | | | 345/173 |
| 2016/0106367 A1 | 4/2016 | Jorov et al. | |
| 2016/0112684 A1* | 4/2016 | Connor | G01N 33/02 |
| | | | 348/158 |
| 2016/0220134 A1 | 8/2016 | Inagaki | |
| 2016/0256082 A1* | 9/2016 | Ely | A61B 5/0024 |
| 2017/0011210 A1* | 1/2017 | Cheong | A61B 5/0022 |
| 2017/0185856 A1* | 6/2017 | Park | G06K 9/00892 |

* cited by examiner

WEARABLE DEVICE AND METHODS OF USING THE SAME

GOVERNMENT SUPPORT

This invention was made with government support under Grant Nos. IIP-1338922, IIS-1213026, CNS-1429345, and CNS-1532061 supported by the National Science Foundation (NSF). The government has certain rights in the invention.

FIELD OF THE INVENTION

Generally disclosed herein is a wearable device that can include one or more finger sensors, one or more wrist sensors, one or more body sensors, a first computer, and an external device. Also disclosed are methods for using the wearable device for inputting the ambient conditions and the movement and bio-signals of a user to an external device.

BACKGROUND

Modern input devices have allowed many new user interaction developments. For example, the inclusion of capacitive touch and motion sensors can provide powerful user interfaces. While most users are accustomed to using their fingers to interact with electronic devices by way of keyboards and computer mice, there are still few input devices that can allow for finger motion inputs without requiring handholding or a specific positioning of the device. In fact, many of these input devices can be cumbersome for mobile uses and for augmented reality and virtual reality systems. Moreover, they can be difficult to use when the person is in a standing position, e.g., a worker in the field or at a construction site.

BRIEF SUMMARY

In view of the above, there is a need for new input devices where the user can make inputs to external devices through finger motions and sensors, which can be used for augmented reality and virtual reality systems, and which are easy to use in more active body positions.

Embodiments of the subject invention provide wearable devices and methods of using the same for input to an external device. In one specific embodiment, a wearable device can include one or more finger sensors and one or more wrist sensors. Each finger sensor can include: one or more accelerometers; one or more gyroscopes; one or more compasses (for example, magnetometers); one or more transceivers; one or more power sources; one or more electrodes; one or more transducers; one or more heartrate monitors; one or more electromyograms; one or more galvanic skin response sensors; one or more electromyography sensors; one or more phonomyography sensors; one or more sweat sensors; one or more Universal Serial Bus (USB) connectors; one or more light sensors; one or more humidity sensors; and/or one or more temperature sensors. Each wrist sensor can include a first computer and one or more touchscreens. Each wrist sensor can further include: one or more accelerometers; one or more gyroscopes; one or more compasses (for example, magnetometers); one or more transceivers; one or more power sources; one or more electrodes; one or more heartrate monitors; one or more galvanic skin response sensors; one or more electromyography sensors; one or more phonomyography sensors; one or more sweat sensors; one or more USB connectors; one or more light sensors; one or more humidity sensors; and/or one or more temperature sensors.

In another specific embodiment, a method can include detecting finger motions of a user with one or more finger sensors, converting the finger motions of the user to digital data, and transmitting the digital data to an external device.

In another specific embodiment, the method can include detecting ambient conditions and movement and bio-signals of a user with one or more finger sensors, converting the ambient conditions and movement and bio-signals of a user to digital data, and transmitting the digital data to an external device.

BRIEF DESCRIPTION OF THE DRAWINGS

FIG. 7 depicts a wearable device according to an embodiment of the subject invention, with the wrist sensor in a bandform factor. One or more environment sensors 720, such as humidity and/or light detectors, are placed on the outer edge of the wrist sensor. A touch screen 710 can be used to interface with the sensors and present data in a user friendly form. A capacitive button 730 can be placed adjacent to the touchscreen and can have a specific function, such as returning to the previous screen or menu. The photoplethysmogram 740 can be placed right at the surface of the wrist sensor and can be separated from the skin, for example, by a piece of glass. Electrodes for the galvanic skin response sensor 715 can be on the bottom. The electrodes can make direct contact with the skin. A motion sensor 760 (e.g., a 9-axis motion sensor) can contain an accelerometer, a gyroscope, and/or a magnetometer and can be placed inside the wrist sensor close to a first computer. Thin electrodes 770 can be made from, for example, one or more printed circuit boards (such as flexible printed circuit boards) can be located on the band and make direct contact with the skin. Low-frequency transducers can be located, for example, right beside the thin electrodes.

DETAILED DISCLOSURE

Embodiments of the subject invention provide wearable devices and methods of using the same for input to an external device. In an embodiment, a wearable device can include one or more finger sensors and one or more wrist sensors. Each finger sensor can include: one or more accelerometers; one or more gyroscopes; one or more compasses (for example, magnetometers); one or more transceivers; one or more power sources; one or more electrodes; one or more transducers; one or more heartrate monitors; one or more electromyograms; one or more galvanic skin response sensors; one or more electromyography sensors; one or more phonomyography sensors; one or more sweat sensors; one or more Universal Serial Bus (USB) connectors; one or more light sensors; one or more humidity sensors; and/or one or more temperature sensors. Each wrist sensor can include a first computer and one or more touchscreens. Each wrist sensor can further include: one or more accelerometers; one or more gyroscopes; one or more compasses (for example, magnetometers); one or more transceivers; one or more power sources; one or more electrodes; one or more heartrate monitors; one or more galvanic skin response sensors; one or more electromyography sensors; one or more phonomyography sensors; one or more sweat sensors; one or more USB connectors; one or more light sensors; one or more humidity sensors; and/or one or more temperature sensors.

In another embodiment, a method can include detecting finger motions of a user with one or more finger sensors, converting the finger motions of the user to digital data, and transmitting the digital data to an external device.

In another embodiment, the method can include detecting ambient conditions and movement and bio-signals of a user with one or more finger sensors, converting the ambient conditions and movement and bio-signals of a user to digital data, and transmitting the digital data to an external device.

Referring to FIGS. 1-7, a wearable device can include, but is not limited to, one or more finger sensors, one or more wrist sensors, one or more body sensors, one or more gloves, and one or more external devices. The wearable device can detect motion and bio-signals of the user with sensors worn at the wrist and the finger, and/or other parts of the body, while serving as a general input device for external devices as well as providing health-related information. The wearable device can allow for the recognition of gestures for the interaction with augmented and virtual reality systems.

The finger sensor can include, for example: one or more accelerometers; one or more gyroscopes; one or more compasses (e.g., magnetometers); one or more transceivers; one or more power sources; one or more printed circuit boards (PCBs) (e.g., one or more flexible PCBs (FPCBs)); one or more electrodes; one or more transducers; one or more heartrate monitors; one or more electromyograms; one or more galvanic skin response sensors; one or more electromyography sensors; one or more phonomyography sensors; one or more sweat sensors; one or more Universal Serial Bus (USB) connectors; one or more light sensors; one or more humidity sensors; and/or one or more temperature sensors. The accelerometer(s), gyroscope(s), and compass(es) (e.g., magnetometer(s)) can be configured to detect the position and motion of the finger of the user. An accelerometer, gyroscope, and magnetometer can be included and form a 9-axis motion sensor to allow for the detection of the orientation of the fingers.

The finger sensor can include different designs and/or form factors. For example, the finger sensor can be in the form of a partially arched structure, ring, and finger sleeve. The finger sensor can have any size inner diameter to fit any size finger of the user. The finger sensor can fit around the proximal phalanges of the user. The glove can fit over the hand of the user and hold the finger sensor and/or wrist sensor in place. The fingers sensors can include any reasonable number of structures (e.g., a number of structures in a range of from 1 to 20).

The wrist sensor can include, for example: one or more accelerometers; one or more gyroscopes; one or more compasses (e.g., magnetometers); one or more transceivers; one or more power sources; a first computer; one or more FPCBs; one or more touchscreens; one or more electrodes; one or more transducers; one or more heartrate monitors; one or more galvanic skin response sensors; one or more electromyography sensors; one or more phonomyography sensors; one or more sweat sensors; one or more USB connectors; one or more light sensors; one or more humidity sensors; and/or one or more temperature sensors. The accelerometer(s), gyroscope(s), and compass(es) (e.g., magnetometer(s)) can be configured to detect the position and motion of the wrist of the user. An accelerometer, gyroscope, and magnetometer can be included and form a 9-axis motion sensor to allow for the detection of the orientation of the fingers.

The wrist sensor can include different designs and/or form factors. For example, the wrist sensor can be in the form of a watch, such as a smartwatch, and a band. The watch and/or band can include a commercially available smartwatch and/or band. The commercially available smartwatch and/or band can be modified with one or more sensors.

In many embodiments, the wrist sensor includes a first computer therein. The first computer can include, for example, a processor, memory, graphical user interface, and a transceiver. The first computer of the wrist sensor can receive user input from the remainder of the wrist sensor, the finger sensor, and/or a body sensor, process the detected signals into user instruction signals based on the identification, and transmit to an external device. The first computer can record the motion and the bio-signal data and use algorithms to detect the motion of the user. The data can be recorded at specific time intervals to ensure that the data is controlled and easily interpreted. The data can also be filtered to provide more accurate sensing. The first computer can include a network circuit enabling it to communicate with an external device through a communicate network. Thus, a user can selectively interact with a variety of external devices from a convenient distance and issue commands by making gestures with the wearable device.

When the wearable device is not concurrently interfacing with the external device, the memory can retain all the information recorded, which can later be transmitted to the external device. For example, global positioning system (GPS) data or heart rate throughout the day can be later sent to the external device. The wearable device can save the information as either compressed data or processed data, such as heart rate at moments in time as opposed to every sample recorded. The wearable device can also allow for expandable storage in the form of a standard device, such as a micro SD card.

Figure 3:
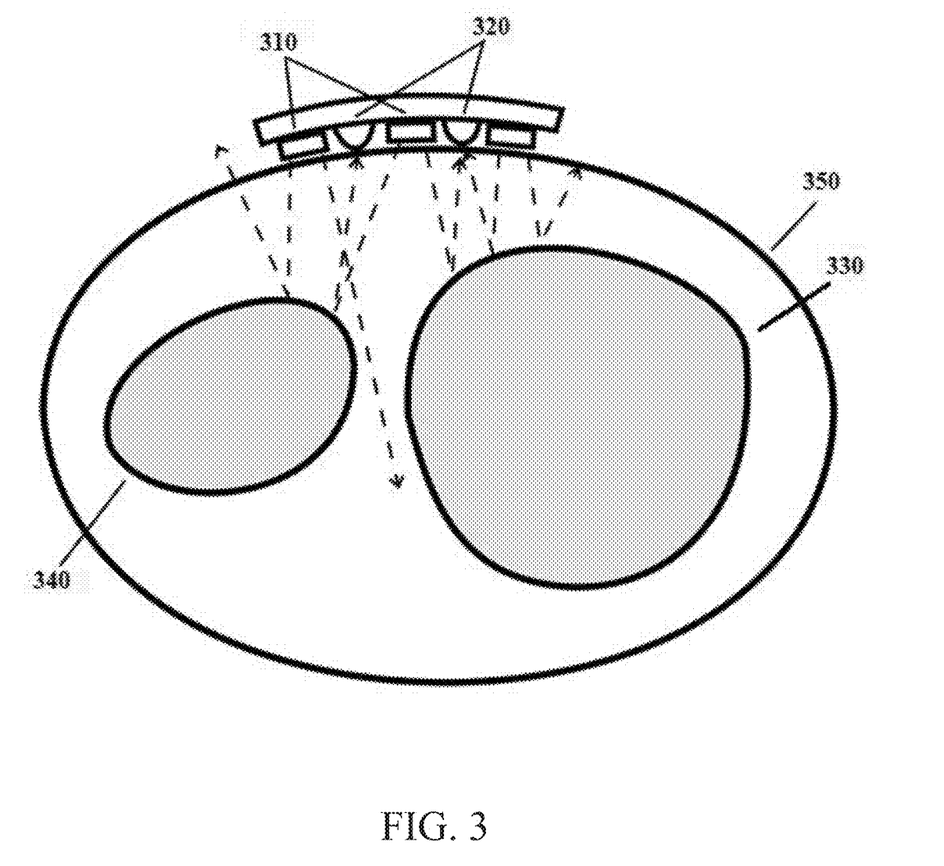
FIG. 3 depicts a photoplethysmogram on a wrist sensor according to an embodiment of the subject invention. The photoplethysmogram projects light though the skin on the wrist 350 using light emitting diodes 310 and measures the reflected light through photosensitive sensors 320. The light can be (completely or mostly) reflected by dense materials like the radius 330 and ulna 340.
Figure 4:
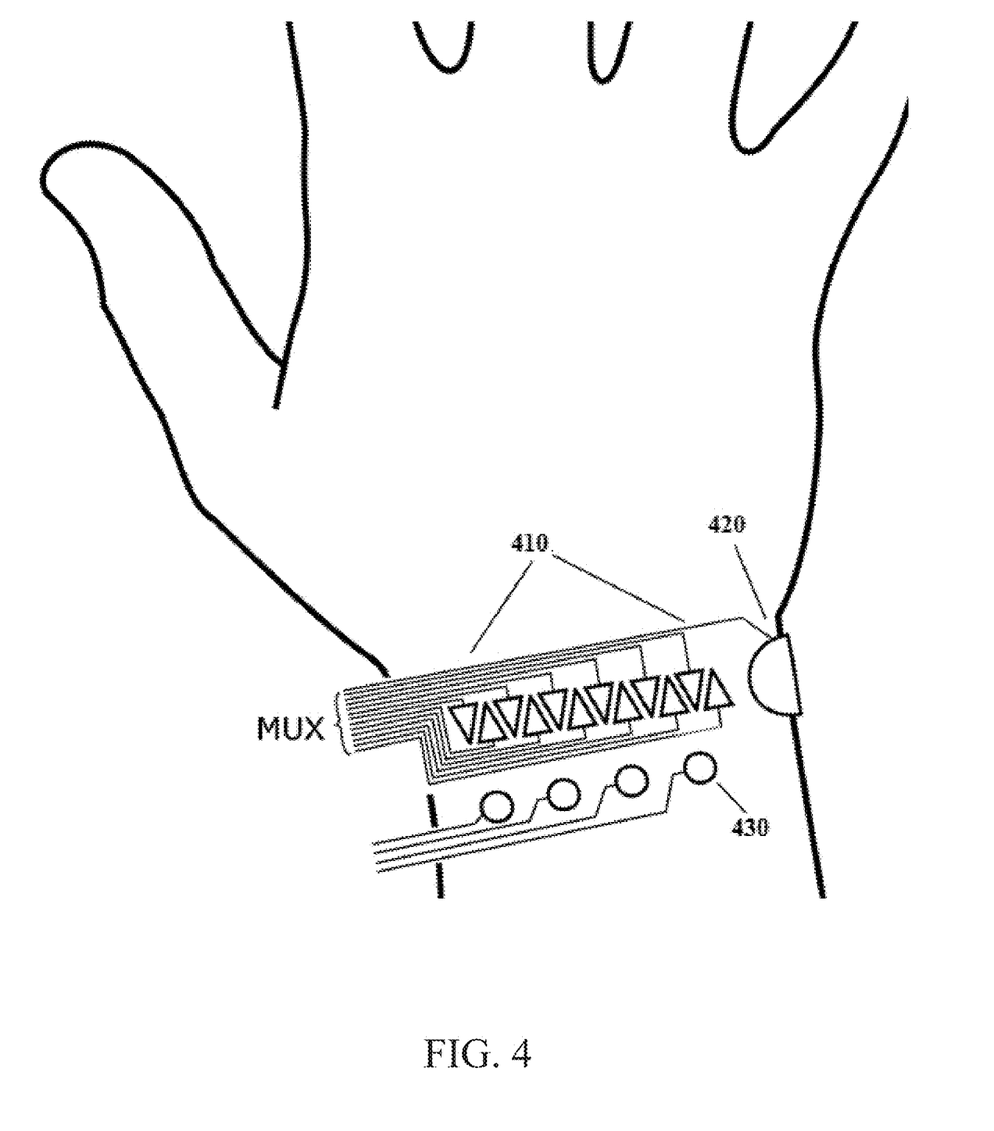
FIG. 4 depicts electrodes 410 on the wrist sensor according to an embodiment of the subject invention. The electrodes are placed above and below the wrist to detect action potential in muscles. A reference electrode 420 on the bone can be used to determine the change in voltage in the electrodes. The outputs can be multiplexed if pins are needed. One or more transducers 430 can be located on the wrist to record low frequency sound/vibrations from the muscles or tendons moving.
Figure 5:
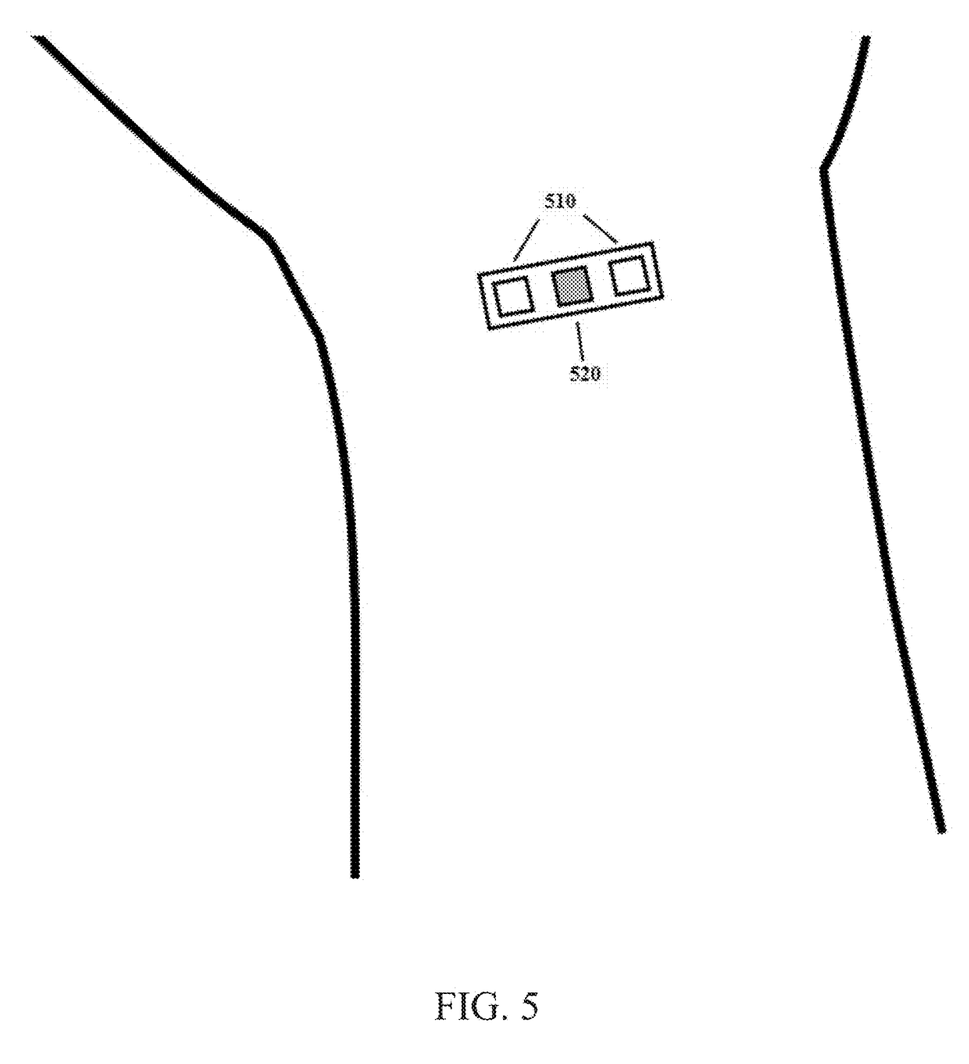
FIG. 5 depicts a photoplethysmogram on the wrist sensor according to an embodiment of the subject invention. The wrist sensor has light emitting diodes 510 and a photoreceptor 520.
Figure 6:
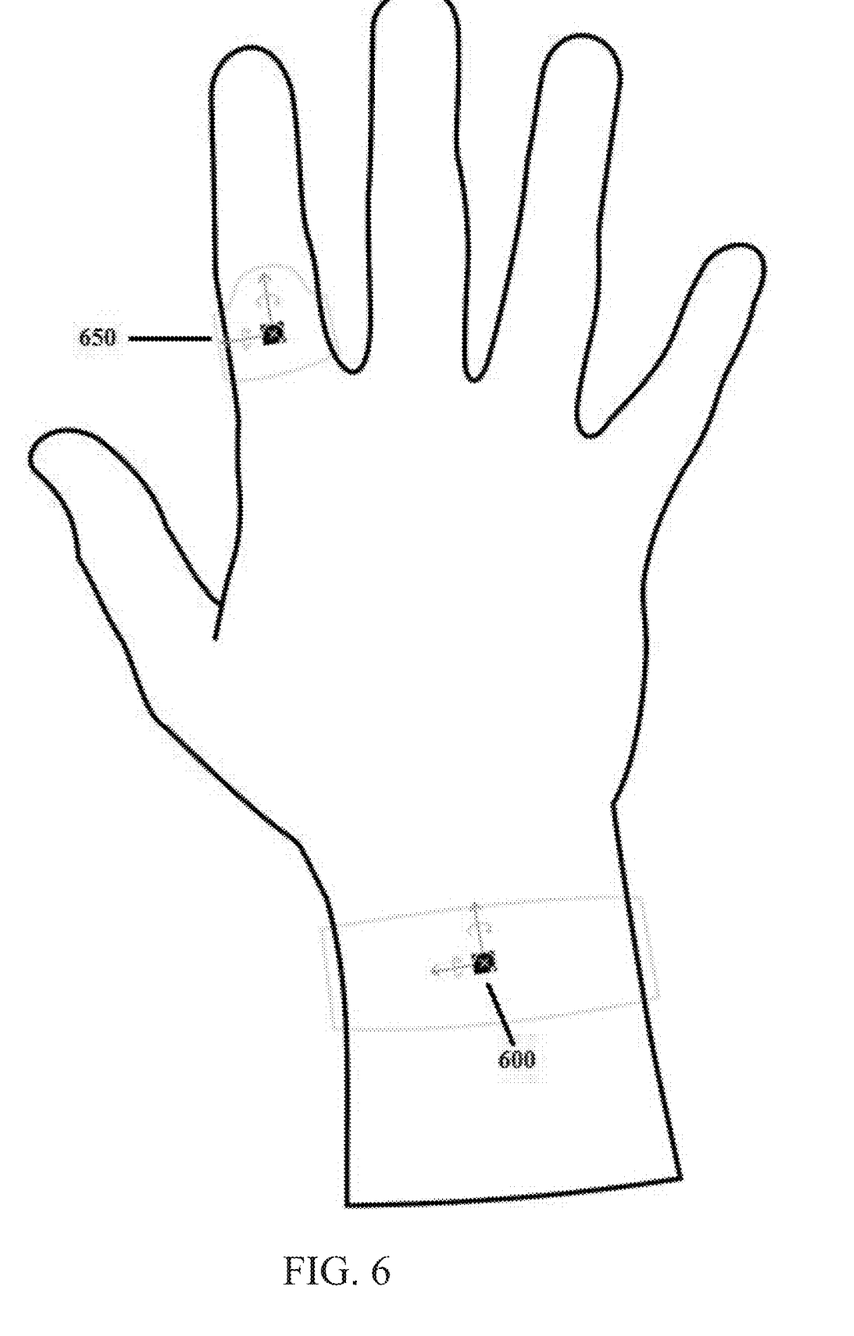
FIG. 6 depicts a wearable device with a motion sensor within a wrist sensor 600 and motion sensor within a finger sensor 650 according to an embodiment of the subject invention.

FIGS. 3 and 5 show a photoplethysmogram or heart rate monitor according to an embodiment of the subject invention. The photoplethysmogram can shine a light into the body using a light emitting diode and determine the returned amount of light using a photosensitive component such as a phototransistor. The blood absorbs certain frequencies of light better than others with the absorption from the hemoglobin being a good source for measurement. As the heart beats more blood is pumped within the measurement area, which decreases the amount of light reflected. Calculating the time between the peaks or troughs of this recorded signal can provide the heart rate. Detecting heart rate can be useful for monitoring health, as well as interfacing with various types of computer software. It could determine stress levels and can be used when exercising to determine how intense a workout is. Used with a program on the first computer that intends to illicit an emotional response can monitor the reaction of the user. General monitoring throughout the day can determine if the user is under some sort of stress with additional data from the motion sensors and galvanic skin response sensor.

Figure 1:
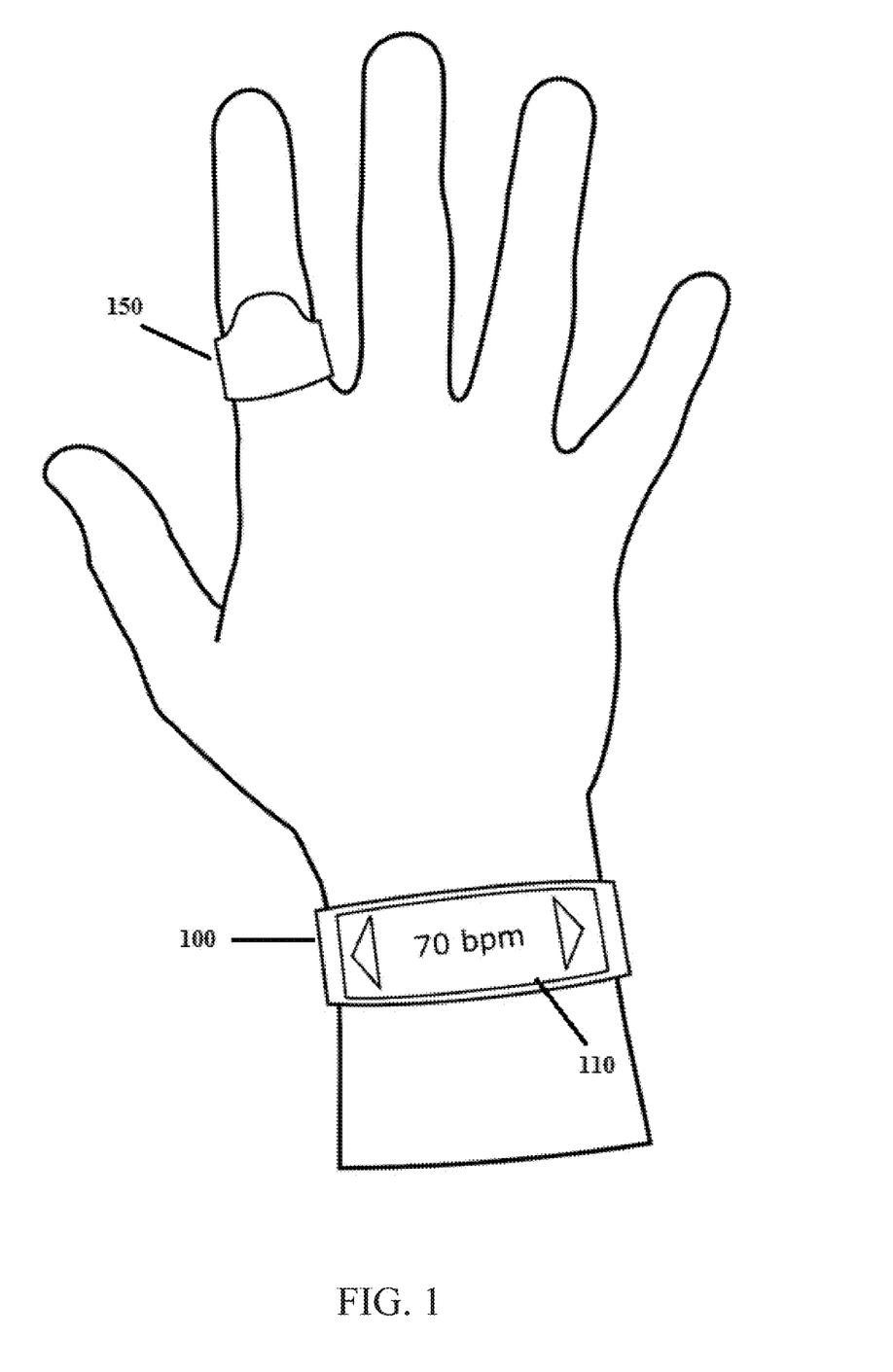
FIG. 1 depicts a wearable device with a wrist sensor 100 in a watch form factor according to an embodiment of the subject invention. On the wrist sensor, a capacitive touchscreen 110 is showing the heart rate of the user. The finger sensor 150 is placed on the index finger of the user.
Figure 2:
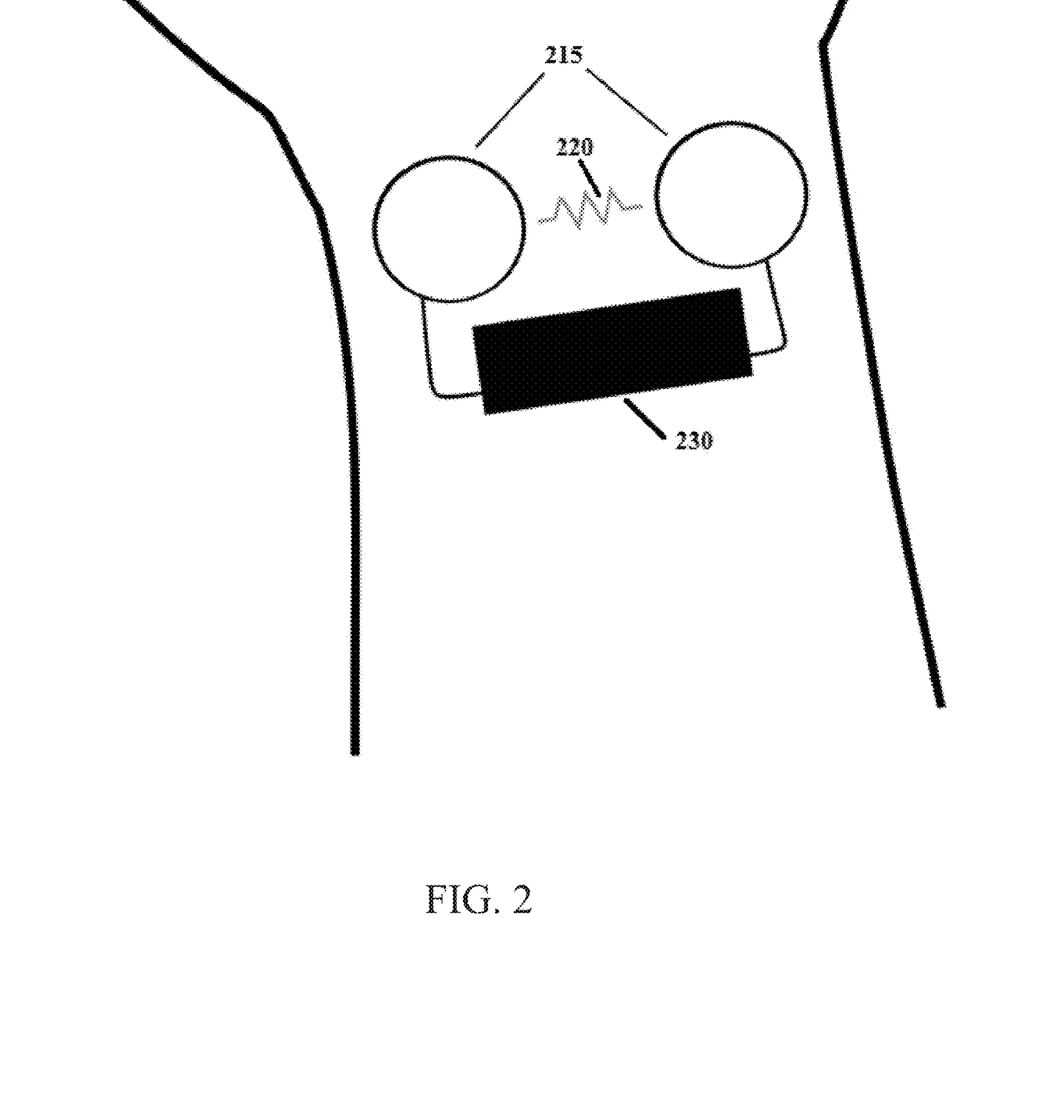
FIG. 2 depicts a galvanic skin response sensor 215 on a wrist sensor with two electrodes and a power supply 230 according to an embodiment of the subject invention. There is a measurable resistance 220 on the skin between the electrodes.

A galvanic skin response is a person's change in skin conductance caused by emotional stress. As a person experiences this emotional stress, they produce a small amount of sweat that is detectable with a galvanic skin response sensor. The galvanic skin response sensor places electrodes on the skin at a fixed distance and passes a current between them. This is shown in FIG. 2. The change in voltage across the skin can be measured as the conductance changes.

The motion of the fingers can be detected from surface electromyograms and phonomyograms. The electromyogram can determine the change in voltage of a muscle as it flexes. Specifically, the flexor digitorum profundus is used for flexing the digits and the flexor pollicis longus is used for flexing the thumb, while the extensor digitorum communis is used for extending the fingers and the extensor pollicis muscles extend the thumb. The electrodes can read a change in voltage that is created by an action potential in the muscles, where ions inside and outside the cell walls move. By using an array of electrodes around the arm where the signals can be read, it can be determined which finger is moving and whether it is flexing or extending. A depiction of the sensors can be seen in FIG. 4. This provides a method for users to "tap" in mid-air and interact with devices along with the use of gesture recognition from movement of the hand. Phonomyography can detect the sound created by the contraction of the muscle. The sound created can be very low in frequency, but can be analyzed with piezoelectric crystals, accelerometers, and low frequency condenser microphones. The recorded sound mixed with the electromyography signal can be combined for more accurate location of muscle contraction, which leads to better detection of finger movement.

Determining the content of a sweat of the user can provide an indication of the general health of the user. For example, sodium, potassium, chlorine, as well as many others can all be detected with sweat sensors, which can determine if someone is dehydrated or detect if someone has a more serious condition, such as cystic fibrosis. The sweat sensors can determine the voltage at electrodes by measuring concentration of ions in the sweat. The electrodes of the sweat sensor can treated with a membrane that only allows a single type of ion to pass. Using electrodes specifically made for each type of ion expected to be found, the contents of the sweat can be monitored independently.

Figure 7:
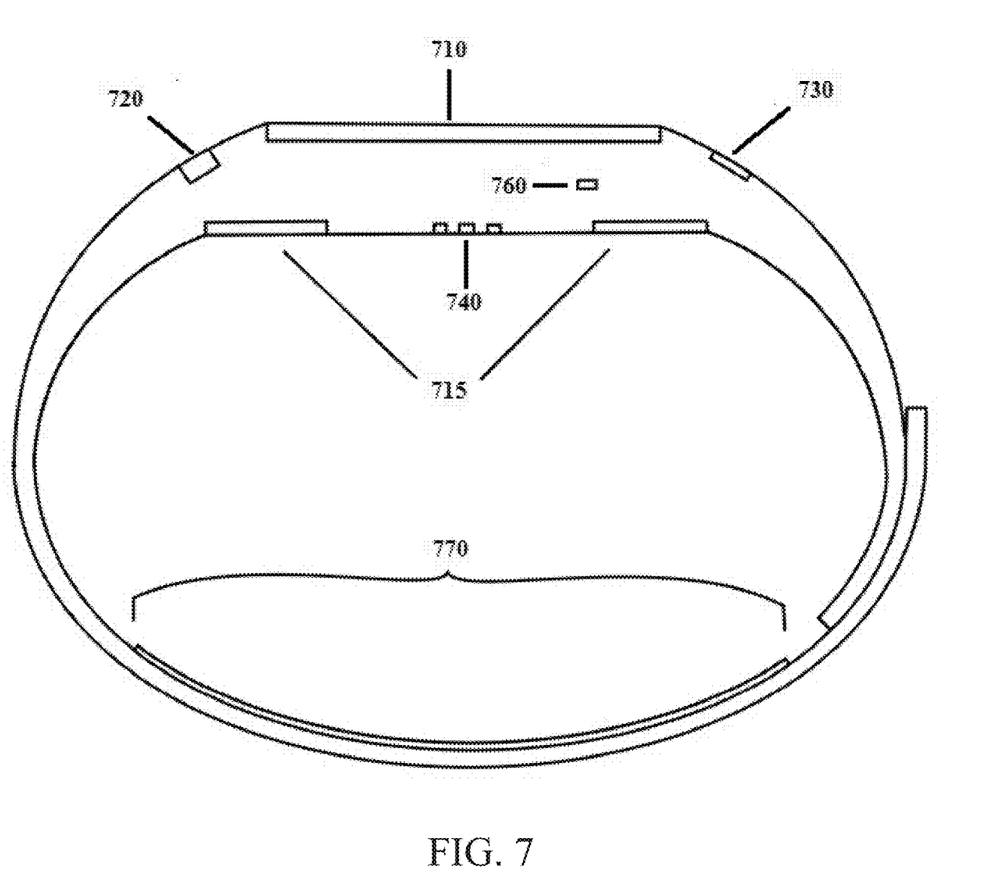

A temperature sensor can be attached to the skin and can detect surface skin temperature. Being able to determine heat under the armpit or in the mouth is a good indicator of core body temperature. Core body temperature can be monitored to determine illnesses such as fevers. Also, by monitoring the ambient temperature around the user, valuable information can be obtained. For example, if a person is much warmer or colder than expected, relative to the environment, then an external device can provide suggestions on actions to take. Temperature sensors, along with other environmental sensors, are shown in FIG. 7.

The body sensors can include, for example: one or more accelerometers; one or more gyroscopes; one or more compasses (e.g., magnetometers); one or more transceivers; one or more power sources; one or more electrodes; one or more transducers; one or more heartrate monitors; one or more galvanic skin response sensors; one or more electromyography sensors; one or more phonomyography sensors; one or more sweat sensors; one or more USB connectors; one or more light sensors; one or more humidity sensors; and/or one or more temperature sensors. The accelerometer(s), gyroscope(s), and compass(es) (e.g., magnetometers(s)) can be configured to detect the position and motion of the body of the user. An accelerometer, gyroscope, and magnetometer can be included and can form a 9-axis sensor or a 3-axis sensor to allow for determination of the orientation of the body.

The external device can be, for example: a second computer, such as a smartphone, desktop, laptop, or tablet; a television; a control panel; a camera; an electrical appliance; and/or a game console. The external device can include commercially available devices. The wearable device can be programmable by a user to associate more or fewer external devices. The wearable device can be capable of identifying an external device upon a user command, or automatically detecting the presence of an associated external device.

In one embodiment, a method for using the wearable device can include, for example: detecting finger motions of a user with one or more finger sensors; converting the finger motions of the user to digital data; and transmitting the digital data to an external device. In another embodiment, a method for using the wearable device can include can include, for example: detecting ambient conditions and movement and bio-signals of a user with one or more finger sensors; converting the ambient conditions and movement and bio-signals of a user to digital data; and transmitting the digital data to an external device.

The accelerometers of the wearable device can detect linear motion along an axis, such as up and down, left and right, and forward and back. The gyroscopes of the wearable device can detect rotation about an axis such as roll, pitch, and yaw. The magnetometers of the wearable device can change their output based on their orientation relative to a magnetic field. They can be used to detect the magnetic field of the Earth, thereby providing the orientation of the wearable device. The 3-axis detection for each finger sensor, wrist sensor, and body sensor allows the detection of movement in three-dimensional space. By placing these sensors on the wrist as well as on the fingers, the detection of the arm movement and finger can also be accomplished. The wearable device can allow for the user to move their fingers in three-dimensional space for input to the external device without the use of a camera by recording change in muscle state.

The wearable device can allow for gesture recognition for both mobile devices and personal computers, as well as for virtual and augmented reality systems. For example, the wearable device can detect gesture input that creates operation information for the external device by detecting the movement of the finger. The finger sensor by providing the accelerometer(s), magnetometer(s), and gyroscope(s) can detect the trajectory of the finger of the user, and can then generate input information to the touchscreen and/or the external device. The finger sensor can be configured to detect the motions of individual fingers such as clicks, shakes, slides, bending, circling, pointing, etc. Motion signals can be generated based on orientation, rotation, speed, and/or relative positions of the fingers. The sensors can collaborate to discern finger motions and/or gestures made by multiple fingers based on the relative positions or position changes of the fingers. A combination of the motion signals detected from multiple fingers may be interpreted as a single user instruction. A series of motions can also be interpreted into a single user instruction based on the trajectory of the fingers. Each associated external device may recognize a different set of user finger motions or gestures. The same motion or gesture may be interpreted as different user instructions depending on the external device receiving it.

The gesture recognition can be completed at the wearable device and/or the external device. Motion sensing can also be used for determining aspects of health. For example, the wearable device can use the motion sensors with the heart rate monitor and galvanic skin response sensor to determine if raising heart rate and sweating is due to physical exertion or emotional stress.

The wearable device can use a global positioning system to track location and distance traveled by the user. When used with external device that has a GPS module, data can simply be retrieved from the external device. If the wearable device is intended to be used without an external GPS, the GPS could be embedded in the device.

The finger sensor, wrist sensor, body sensor, and/or the external devices can transmit data to each other through flexible wires or through wireless communication channels. The wireless communication channels can include, but is not limited to, wireless radio, WI-FI®, BLUETOOTH®, and ZIGBEE®. The wrist sensor of the wearable device can act as a master with the finger sensors as slaves. A body sensor or another wrist sensor can be added to the wearable device to improve the user response.

The various sensors of the wearable device can work without any input of the user or the user can use the touchscreen to enter input for the wearable device and/or the external device. For example, the touchscreen can be used to accept or deny a request from the external device, access battery saving features, connect with BLUETOOTH®, among other functions and can display a clock, heart rate, or current temperature.

The power supply or supplies for the wearable device can be rechargeable and/or replaceable. Each power supply can be, for example, a lithium ion battery and/or nickel cadmium battery. The wearable device can be charged wirelessly. Using a charging pad that is plugged into a wall outlet, the wearable device can be placed on top and have a charge induced to the power supply. The energy can be saved in a rechargeable power supply. Wireless charging provides can provide ease of use for the owner and removing the charging port reduces the number of openings the device has, thereby limiting the possibility of water damage.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A wearable device, comprising:
a finger sensor (configured to be worn on a user's finger); and
a wrist sensor (configured to be worn on a user's wrist),
the finger sensor comprising a first accelerometer, a first gyroscope, and a first magnetometer,
the wrist sensor comprising a first computing device, a wrist sensor power source, a display, a second accelerometer, a second gyroscope, and a second magnetometer.

Embodiment 2

The wearable device according to embodiment 1, the finger sensor further comprising a first compass (e.g., a first magnetometer).

Embodiment 3

The wearable device according to any of embodiments 1-2, the wrist sensor further comprising a second compass (e.g., a second magnetometer).

Embodiment 4

The wearable device according to any of embodiments 1-3, the finger sensor further comprising a first transceiver.

Embodiment 5

The wearable device according to any of embodiments 1-4, the wrist sensor further comprising a second transceiver.

Embodiment 6

The wearable device according to any of embodiments 1-5, the display being a touchscreen.

Embodiment 7

The wearable device according to any of embodiments 1-6, the finger sensor comprising a plurality of first accelerometers.

Embodiment 8

The wearable device according to any of embodiments 1-7, the finger sensor comprising a plurality of first gyroscopes.

Embodiment 9

The wearable device according to any of embodiments 1-8, the finger sensor comprising a plurality of first magnetometers.

Embodiment 10

The wearable device according to any of embodiments 1-9, the wrist sensor comprising a plurality of second accelerometers.

Embodiment 11

The wearable device according to any of embodiments 1-10, the wrist sensor comprising a plurality of second gyroscopes.

Embodiment 12

The wearable device according to any of embodiments 1-11, the wrist sensor comprising a plurality of second magnetometers.

Embodiment 13

The wearable device according to any of embodiments 1-12, the wrist sensor comprising a plurality of first computing devices.

Embodiment 14

The wearable device according to any of embodiments 1-13, the wrist sensor comprising a plurality of wrist sensor power sources.

Embodiment 15

The wearable device according to any of embodiments 1-13, the wrist sensor comprising a plurality of displays.

Embodiment 16

The wearable device according to any of embodiments 2-15, the finger sensor comprising a plurality of first compasses (e.g., first magnetometers).

Embodiment 17

The wearable device according to any of embodiments 3-16, the wrist sensor comprising a plurality of second compasses (e.g., second magnetometers).

Embodiment 18

The wearable device according to any of embodiments 4-17, the finger sensor comprising a plurality of first transceivers.

Embodiment 19

The wearable device according to any of embodiments 5-18, the wrist sensor comprising a plurality of second transceivers.

Embodiment 20

The wearable device according to any of embodiments 1-19, the finger sensor further comprising at least one of the following: a finger sensor power source; a first electrode; a first transducer; a first flexible printed circuit board (FPCB); a first heartrate monitor; a first electromyogram; a first galvanic skin response sensor; a first electromyography sensor; a first phonomyography sensor; a first sweat sensor; a first Universal Serial Bus (USB) connector; a first light sensor; a first humidity sensor; and a first temperature sensor.

Embodiment 21

The wearable device according to any of embodiments 1-20, the wrist sensor further comprising at least one of the following: a second electrode; a second transducer; a second FPCB; a second heartrate monitor; a second electromyogram; a second galvanic skin response sensor; a second electromyography sensor; a second phonomyography sensor; a second sweat sensor; a second USB connector; a second light sensor; a second humidity sensor; and a second temperature sensor.

Embodiment 22

The wearable device according to any of embodiments 1-21, the finger sensor further comprising at least one of the following: a plurality of finger sensor power sources; a plurality of first electrodes; a plurality of first transducers; a plurality of first flexible printed circuit boards (FPCBs); a plurality of first heartrate monitors; a plurality of first electromyograms; a plurality of first galvanic skin response sensors; a plurality of first electromyography sensors; a plurality of first phonomyography sensors; a plurality of first sweat sensors; a plurality of first Universal Serial Bus (USB) connectors; a plurality of first light sensors; a plurality of first humidity sensors; and a plurality of first temperature sensors.

Embodiment 23

The wearable device according to any of embodiments 1-22, the wrist sensor further comprising at least one of the following: a plurality of second electrodes; a plurality of second transducers; a plurality of second FPCBs; a plurality of second heartrate monitors; a plurality of second electromyograms; a plurality of second galvanic skin response sensors; a plurality of second electromyography sensors; a plurality of second phonomyography sensors; a plurality of second sweat sensors; a plurality of second USB connectors; a plurality of second light sensors; a plurality of second humidity sensors; and a plurality of second temperature sensors.

Embodiment 24

The wearable device according to any of embodiments 1-23, further comprising an external device, the external device being: a smartphone; a desktop; a laptop; a tablet; a television; a control panel; a camera; an electrical appliance; or a game console.

Embodiment 25

The wearable device according to any of embodiments 1-24, further comprising a body sensor (configured to be worn on a location of a user's body other than a finger or wrist),
the body sensor comprising a third accelerometer, a third gyroscope, and a third magnetometer.

Embodiment 26

The wearable device according to embodiment 25, the body sensor further comprising a third compass (e.g., third magnetometer).

Embodiment 27

The wearable device according to any of embodiments 25-26, the body sensor further comprising a third transceiver.

Embodiment 28

The wearable device according to any of embodiments 25-27, the body sensor further comprising at least one of the following: a body sensor power source; a third electrode; a third transducer; a third FPCB; a third heartrate monitor; a third electromyogram; a third galvanic skin response sensor; a third electromyography sensor; a third phonomyography sensor; a third sweat sensor; a third USB connector; a third light sensor; a third humidity sensor; and a third temperature sensor.

Embodiment 29

The wearable device according to any of embodiments 26-28, the body sensor comprising a plurality of third compasses (e.g., third magnetometers).

Embodiment 30

The wearable device according to any of embodiments 27-29, the body sensor comprising a plurality of third transceivers.

Embodiment 31

The wearable device according to any of embodiments 25-30, the body sensor further comprising at least one of the following: a plurality of third electrodes; a plurality of third transducers; a plurality of third FPCBs; a plurality of third heartrate monitors; a plurality of third electromyograms; a plurality of third galvanic skin response sensors; a plurality of third electromyography sensors; a plurality of third phonomyography sensors; a plurality of third sweat sensors; a plurality of third USB connectors; a plurality of third light sensors; a plurality of third humidity sensors; and a plurality of third temperature sensors.

Embodiment 32

The wearable device according to any of embodiments 1-31, further comprising a glove having the finger sensor disposed thereon or therein.

Embodiment 33

The wearable device according to any of embodiments 1-32, comprising a plurality of finger sensors.

Embodiment 34

The wearable device according to any of embodiments 1-33, comprising a plurality of wrist sensors.

Embodiment 35

The wearable device according to any of embodiments 1-34, comprising a plurality of body sensors.

Embodiment 36

A method of inputting user instructions to an external device, the method comprising:
detecting finger motions of a user with a finger sensor of a wearable device, the finger sensor comprising a first accelerometer, a first gyroscope, and a first magnetometer;
converting the finger motions of the user to digital data; and
transmitting the digital data to the external device.

Embodiment 37

The method according to embodiment 36, the external device being: a smartphone; a desktop; a laptop; a tablet; a television; a control panel; a camera; an electrical appliance; or a game console.

Embodiment 38

The method according to any of embodiments 36-37, the finger sensor further comprising a first compass (e.g., first magnetometer).

Embodiment 39

The method according to any of embodiments 36-38, the finger sensor further comprising a first transceiver.

Embodiment 40

The method according to any of embodiments 36-39, the finger sensor comprising a plurality of first accelerometers.

Embodiment 41

The method according to any of embodiments 36-40, the finger sensor comprising a plurality of first gyroscopes.

Embodiment 42

The method according to any of embodiments 36-41, the finger sensor comprising a plurality of first magnetometers.

Embodiment 43

The method according to any of embodiments 38-42, the finger sensor comprising a plurality of first compasses (e.g., first magnetometers).

Embodiment 44

The method according to any of embodiments 39-43, the finger sensor comprising a plurality of first transceivers.

Embodiment 45

The method according to any of embodiments 36-44, the finger sensor further comprising at least one of the following: a finger sensor power source; a first electrode; a first transducer; a first flexible printed circuit board (FPCB); a first heartrate monitor; a first electromyogram; a first galvanic skin response sensor; a first electromyography sensor; a first phonomyography sensor; a first sweat sensor; a first Universal Serial Bus (USB) connector; a first light sensor; a first humidity sensor; and a first temperature sensor.

Embodiment 46

The method according to any of embodiments 36-45, the finger sensor further comprising at least one of the following: a plurality of finger sensor power sources; a plurality of first electrodes; a plurality of first transducers; a plurality of first flexible printed circuit boards (FPCBs); a plurality of first heartrate monitors; a plurality of first electromyograms; a plurality of first galvanic skin response sensors; a plurality of first electromyography sensors; a plurality of first phonomyography sensors; a plurality of first sweat sensors; a plurality of first Universal Serial Bus (USB) connectors; a plurality of first light sensors; a plurality of first humidity sensors; and a plurality of first temperature sensors.

Embodiment 47

The method according to any of embodiments 36-46, the wearable device comprising a plurality of finger sensors.

Embodiment 48

The method according to any of embodiments 36-47, the wearable device being that of any of embodiments 1-35.

Embodiment 49

The method according to any of embodiments 36-48, the detecting finger motions of the user comprising measuring a muscle movement of a finger of the user having the finger sensor worn thereon.

Embodiment 50

The method according to any of embodiments 36-49, further comprising detecting wrist motions of the user with a wrist sensor of the wearable device, the wrist sensor comprising a first computing device, a wrist sensor power source, a second accelerometer, a second gyroscope, and a second magnetometer.

Embodiment 51

The method according to any of embodiments 36-50, further comprising detecting body motions of the user with a body sensor of the wearable device configured to be worn on a location of the user's body other than a finger or wrist, the body sensor comprising a third accelerometer, a third gyroscope, and a third magnetometer.

Embodiment 52

The method according to any of embodiments 36-52, the wearable device further comprising a glove having the finger sensor disposed thereon or therein.

Embodiment 53

A method of inputting movement and bio-signals of a user and ambient conditions to an external device, the method comprising:
 detecting ambient conditions and movement and bio-signals of the user with a wearable device, the wearable device comprising a finger sensor worn on a finger of the user and a wrist sensor worn on a wrist of the user, the finger sensor comprising a first accelerometer, a first gyroscope, and a first magnetometer, and the wrist sensor comprising a first computing device, a wrist sensor power source, a second accelerometer, a second gyroscope, and a second magnetometer;
 converting the ambient conditions and movement and bio-signals of the user to digital data; and
 transmitting the digital data to the external device.

Embodiment 54

The method according to embodiment 53, the external device being: a smartphone; a desktop; a laptop; a tablet; a television; a control panel; a camera; an electrical appliance; or a game console.

Embodiment 55

The method according to any of embodiments 53-54, the wearable device further comprising a body sensor worn on a location of the user other than a finger or wrist, the body sensor comprising a third accelerometer, a third gyroscope, and a third magnetometer.

Embodiment 56

The method according to any of embodiments 53-55, the movement and bio-signals including at least one of: muscle contraction of the finger having the finger sensor thereon; muscle movement; heart rate; sweat composition; galvanic skin response; and body temperature.

Embodiment 57

The method according to any of embodiments 53-56, the ambient conditions including at least one of: temperature; light; and humidity.

Embodiment 58

The method according to any of embodiments 53-57, the wearable device further comprising a glove having the finger sensor disposed thereon or therein.

Embodiment 59

The method according to any of embodiments 53-58, the wearable device being that of any of embodiments 1-35.

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". As used herein, use of the term "including" as well as other forms, such as "includes," and "included," is not limiting. Where reference to an element is "one or more", there can be any reasonable number of elements, such as 1, 2, 3, 4, 5, 6, 7, 8, 9, 10, or more elements.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section, if present) are incorporated by reference in their entirety, including all figures and tables, to the extent they are not inconsistent with the explicit teachings of this specification.

We claim:

1. A wearable device, comprising:
a finger sensor configured to be worn on a user's finger; and
a wrist sensor configured to be worn on a user's wrist,
the finger sensor comprising a first accelerometer, a first gyroscope, a first magnetometer, a first electromyography sensor, a first phonomyography sensor, and a first flexible printed circuit board (FPCB),
the wrist sensor comprising a first computing device, a wrist sensor power source, a display, a second accelerometer, a second gyroscope, and a second magnetometer,
the finger sensor configured to serve as a slave,
the wrist sensor configured to receive an input and serve as a master,
the first electromyography sensor configured to determine a change in a voltage of a muscle and produce an electromyography signal,
the first phonomyography sensor configured to detect a sound created in the muscle,
the wearable device configured to mix the electromyography signal and the sound, and to record the sound mixed with the electromyography signal,
the wrist sensor further comprising an array of electrodes configured to detect a change in voltage created by an action potential in a muscle, a multiplexer connected to the electrodes, a reference electrode disposed in a position such that it corresponds to a bone, a transducer recording low frequency sound, two light emitting diodes, a photosensitive sensor disposed between the two light emitting diodes, and a second FPCB, and
the wrist sensor configured to determine a change in voltage of the array of electrodes based on the reference electrode.

2. The wearable device according to claim 1, the finger sensor further comprising a first compass, and
the wrist sensor further comprising a second compass.

3. The wearable device according to claim 1, the finger sensor further comprising a first transceiver, and
the wrist sensor further comprising a second transceiver.

4. The wearable device according to claim 1, the display being a touchscreen.

5. The wearable device according to claim 1, the finger sensor further comprising all of the following: a first electrode; a first heart rate monitor; a first galvanic skin response sensor; a first sweat sensor; a first Universal Serial Bus (USB) connector; a first light sensor; and a first humidity sensor.

6. The wearable device according to claim 1, the wrist sensor further comprising all of the following: a second galvanic skin response sensor; a second electromyography sensor; a second phonomyography sensor; a second sweat sensor; a second USB connector; a second humidity sensor; and a second temperature sensor.

7. The wearable device according to claim 1, further comprising an external device, the external device being: a smartphone; a desktop; a laptop; a tablet; a television; a control panel; a camera; an electrical appliance; or a game console.

8. The wearable device according to claim 1, further comprising a body sensor configured to be worn on a location of a user's body other than a finger or wrist,
the body sensor comprising a third accelerometer, a third gyroscope, and a third magnetometer.

9. The wearable device according to claim 8, the body sensor further comprising a third compass.

10. The wearable device according to claim 8, the body sensor further comprising at least one of the following: a body sensor power source; a third transceiver; a third electrode; a third transducer; a third FPCB; a third heartrate monitor; a third galvanic skin response sensor; a third electromyography sensor; a third phonomyography sensor; a third sweat sensor; a third USB connector; a third light sensor; a third humidity sensor; and a third temperature sensor.

11. The wearable device according to claim 1, further comprising a glove having the finger sensor disposed thereon or therein.

12. A method of inputting user instructions to an external device, the method comprising:
detecting finger motions of a user from a voltage and a sound of a muscle with a finger sensor of a wearable device, the finger sensor comprising a first accelerometer, a first gyroscope, a first magnetometer, a first electromyography sensor, a first phonomyography sensor, and a first flexible printed circuit board (FPCB), the first electromyography sensor determining a change of the voltage of the muscle and producing an electromyography signal, the first phonomyography sensor detecting a sound created in the muscle, the electromyography signal and the sound being mixed, and the sound mixed with the electromyography signal being recorded;
detecting wrist motions of the user with a wrist sensor of the wearable device, the wrist sensor comprising a first computing device, a wrist sensor power source, a display, a second accelerometer, a second gyroscope, a second magnetometer, an array of electrodes configured to detect a change in voltage created by an action potential in a muscle, a multiplexer connected to the electrodes, a reference electrode disposed in a position such that it corresponds to a bone, a transducer recording low frequency sound, two light emitting diodes configured to project a light, a photosensitive sensor disposed between the two light emitting diodes and configured to receive a reflected light of the projected light, and a second FPCB, the wrist sensor determining a change in voltage of the array of electrodes based on the reference electrode;

converting the finger motions and wrist motions of the user to digital data; and transmitting the digital data to the external device, the external device being: a smartphone; a desktop; a laptop; a tablet; a television; a control panel; a camera; an electrical appliance; or a game console.

13. The method according to claim 12, the wearable device further comprising a glove having the finger sensor disposed thereon or therein.

14. The method according to claim 12, the detecting finger motions of the user comprising measuring a muscle movement of a finger of the user having the finger sensor worn thereon.

15. The method according to claim 12, further comprising detecting body motions of the user with a body sensor of the wearable device configured to be worn on a location of the user's body other than a finger or wrist, the body sensor comprising a third accelerometer, a third gyroscope, and a third magnetometer.

16. The method according to claim 12, the finger sensor further comprising all of the following: a first electrode; a first heartrate monitor; a first galvanic skin response sensor; a first sweat sensor; a first Universal Serial Bus (USB) connector; a first light sensor; and a first humidity sensor, and the wrist sensor further comprising all of the following: a second galvanic skin response sensor; a second electromyography sensor; a second phonomyography sensor; a second sweat sensor; a second USB connector; a second humidity sensor; and a second temperature sensor.

17. A method of inputting movement and bio-signals of a user and ambient conditions to an external device, the method comprising:

detecting ambient conditions and movement and bio-signals of the user with a wearable device, the wearable device comprising a finger sensor worn on a finger of the user and a wrist sensor worn on a wrist of the user, the finger sensor comprising a first accelerometer, a first gyroscope, a first magnetometer, a first electromyography sensor, a first phonomyography sensor, and a first flexible printed circuit board (FPCB), and the wrist sensor comprising a first computing device, a wrist sensor power source, a display, a second accelerometer, a second gyroscope, a second magnetometer, an array of electrodes configured to detect a change in voltage created by an action potential in a muscle, a multiplexer connected to the electrodes, a reference electrode disposed in a position such that it corresponds to a bone, a transducer recording low frequency sound, two light emitting diodes configured to project a light, a photosensitive sensor disposed between the two light emitting diodes and configured to receive a reflected light of the projected light, and a second FPCB;

converting the ambient conditions and movement and bio-signals of the user to digital data; and transmitting the digital data to the external device, the external device being: a smartphone; a desktop; a laptop; a tablet; a television; a control panel; a camera; an electrical appliance; or a game console, the wrist sensor serving as a master by receiving an input from the user, and the finger sensor serving as a slave, the first electromyography sensor determining a change in a voltage of a muscle and producing an electromyography signal, the first phonomyography sensor detecting a sound created in the muscle, the wearable device mixing the electromyography signal and the sound, and recording the sound mixed with the electromyography signal, and the wrist sensor determining a change in voltage of the array of electrodes based on the reference electrode.

18. The method according to claim 17, the wearable device further comprising a body sensor worn on a location of the user other than a finger or wrist, the body sensor comprising a third accelerometer, a third gyroscope, and a third magnetometer, the movement and bio-signals including at least one of: muscle contraction of the finger having the finger sensor thereon; muscle movement; heart rate; sweat composition; galvanic skin response; and body temperature, and the ambient conditions including at least one of: temperature; light; and humidity.

19. The method according to claim 17, the wearable device further comprising a glove having the finger sensor disposed thereon or therein.

20. The method according to claim 17, the finger sensor further comprising all of the following: a first electrode; a first heartrate monitor; a first galvanic skin response sensor; a first sweat sensor; a first Universal Serial Bus (USB) connector; a first light sensor; and a first humidity sensor, and the wrist sensor further comprising all of the following: a second galvanic skin response sensor; a second electromyography sensor; a second phonomyography sensor; a second sweat sensor; a second USB connector; a second humidity sensor; and a second temperature sensor.

* * * * *